United States Patent
Marcovici (10) Patent No.: US 9,730,659 B2
(45) Date of Patent: Aug. 15, 2017

(54) MULTI-MODALITY IMAGE ACQUISITION

(75) Inventor: Sorin Marcovici, Lexington, MA (US)

(73) Assignee: ANALOGIC CORPORATION, Peabody, MA (US)

(*) Notice: Subject to any disclaimer, the term of this patent is extended or adjusted under 35 U.S.C. 154(b) by 0 days.

(21) Appl. No.: 13/885,445

(22) PCT Filed: Nov. 16, 2010

(86) PCT No.: PCT/US2010/056855
§ 371 (c)(1),
(2), (4) Date: May 15, 2013

(87) PCT Pub. No.: WO2012/067607
PCT Pub. Date: May 24, 2012

(65) Prior Publication Data
US 2013/0237814 A1    Sep. 12, 2013

(51) Int. Cl.
*A61B 6/00* (2006.01)
*A61B 6/04* (2006.01)
(Continued)

(52) U.S. Cl.
CPC .......... *A61B 6/4417* (2013.01); *A61B 6/025* (2013.01); *A61B 6/04* (2013.01); *A61B 6/0414* (2013.01);
(Continued)

(58) Field of Classification Search
CPC ......... A61B 6/025; A61B 6/04; A61B 6/0414; A61B 6/4417; A61B 6/4435; A61B 6/502;
(Continued)

(56) References Cited

U.S. PATENT DOCUMENTS 4,352,486 A * 10/1982 Hixenbaugh .......... F27D 21/00 266/89
4,478,084 A  10/1984 Hassler et al.
(Continued)

FOREIGN PATENT DOCUMENTS

| EP | 1977692 A2 | 10/2008 |
| JP | 2008272459 A | 11/2008 |
| JP | 2015125080 A | 7/2015 |
| WO | 0009014 | 2/2000 |

OTHER PUBLICATIONS

Non-Final Office Action cited in U.S. Appl. No. 12/345,080 dated Aug. 3, 2010, 10 pgs.
(Continued)

*Primary Examiner* — Ruth S Smith
(74) *Attorney, Agent, or Firm* — Cooper Legal Group, LLC (57) ABSTRACT

One or more techniques and/or systems described herein provide for generating a radiographic image and ultrasound image depicting parallel planes of an object under examination and may be used in conjunction with radiographic or ultrasound techniques known to those in the field (e.g., x-ray tomosynthesis, computed tomography ultrasound imaging, etc.). An ultrasound frontend component is configured to transmit ultrasound waves in a direction substantially parallel to a trajectory of radiation. In one example, one or more radiographic images of an object are spatially coincident to one or more ultrasound images of the object in the same position and/or geometric shape/volume, and the images may be combined to generate a combined image depicting features of the ultrasound image (e.g., the sensitivity of the ultrasound image) and features of the radiographic image (e.g., the morphological details of the radiographic image).

20 Claims, 5 Drawing Sheets (51) Int. Cl.
*A61B 8/08* (2006.01)
*A61B 8/00* (2006.01)
*A61B 6/02* (2006.01)
*A61B 8/13* (2006.01)

(52) U.S. Cl.
CPC ............ *A61B 6/4435* (2013.01); *A61B 6/502* (2013.01); *A61B 6/5247* (2013.01); *A61B 8/0825* (2013.01); *A61B 8/13* (2013.01); *A61B 8/403* (2013.01); *A61B 8/4416* (2013.01); *A61B 8/4477* (2013.01); *A61B 8/5207* (2013.01); *A61B 8/5261* (2013.01)

(58) Field of Classification Search
CPC ....... A61B 6/5247; A61B 8/0825; A61B 8/13; A61B 8/403; A61B 8/4416; A61B 8/4477; A61B 8/5207; A61B 8/5261
See application file for complete search history.

(56) References Cited

U.S. PATENT DOCUMENTS

| | | | |
|---|---|---|---|
| 5,868,673 | A | 2/1999 | Vesely |
| 5,872,828 | A * | 2/1999 | Niklason ................ A61B 6/025 378/23 |
| 5,938,613 | A | 8/1999 | Shmulewitz |
| 6,074,489 | A | 6/2000 | Morano |
| 6,385,474 | B1 | 5/2002 | Rather et al. |
| 6,396,940 | B1 | 5/2002 | Carrott et al. |
| 6,450,960 | B1 | 9/2002 | Rather et al. |
| 6,540,678 | B2 | 4/2003 | Rather et al. |
| 6,607,489 | B2 | 8/2003 | Hoctor et al. |
| 6,672,165 | B2 | 1/2004 | Rather et al. |
| 6,728,567 | B2 | 4/2004 | Rather et al. |
| 6,837,854 | B2 | 1/2005 | Moore et al. |
| 6,926,672 | B2 | 8/2005 | Moore et al. |
| 6,984,210 | B2 | 1/2006 | Chambers et al. |
| 7,285,092 | B2 | 10/2007 | Duric et al. |
| 2002/0099290 | A1 | 7/2002 | Haddad |
| 2003/0007598 | A1 | 1/2003 | Wang et al. |
| 2003/0072417 | A1 | 4/2003 | Kaufhold et al. |
| 2003/0153830 | A1 * | 8/2003 | Weinberg et al. ............ 600/436 |
| 2003/0167004 | A1 | 9/2003 | Dines et al. |
| 2004/0030277 | A1 | 2/2004 | O'Mahony et al. |
| 2004/0068170 | A1 | 4/2004 | Wang et al. |
| 2004/0249271 | A1 | 12/2004 | Besson et al. |
| 2005/0089205 | A1 | 4/2005 | Kapur et al. |
| 2005/0100129 | A1 | 5/2005 | McKenna |
| 2005/0288581 | A1 | 12/2005 | Kapur et al. |
| 2006/0173304 | A1 | 8/2006 | Wang |
| 2007/0003117 | A1 | 1/2007 | Wheeler et al. |
| 2007/0156047 | A1 | 7/2007 | Nagler et al. |
| 2008/0045833 | A1 | 2/2008 | Defreitas et al. |
| 2008/0101530 | A1 | 5/2008 | Ullberg et al. |
| 2008/0175408 | A1 | 7/2008 | Mukund et al. |
| 2008/0234578 | A1 | 9/2008 | Claus |
| 2008/0242979 | A1 * | 10/2008 | Fisher et al. .................. 600/427 |
| 2008/0249415 | A1 * | 10/2008 | Okamura ............ A61B 6/0414 600/445 |
| 2009/0183350 | A1 * | 7/2009 | Wulf .................... B06B 1/0622 29/402.08 |
| 2009/0290679 | A1 | 11/2009 | Mikami et al. |
| 2009/0316854 | A1 | 12/2009 | Ismail et al. |
| 2010/0111379 | A1 | 5/2010 | Suri et al. |
| 2010/0166147 | A1 | 7/2010 | Abenaim |
| 2011/0295115 | A1 * | 12/2011 | Yarnall .......................... 600/436 |

OTHER PUBLICATIONS

Reply Non-Final Office Action cited in U.S. Appl. No. 12/345,080 dated Nov. 3, 2010, 9 pgs.
Non-Final Office Action cited in U.S. Appl. No. 12/345,080 dated Jan. 21, 2011, 20 pgs.
Reply Non-Final Office Action cited in U.S. Appl. No. 12/345,080 dated Apr. 21, 2011, 18 pgs.
Final Office Action cited in U.S. Appl. No. 12/345,080 dated Jul. 21, 2011, 22 pgs.
Reply Final Office Action cited in U.S. Appl. No. 12/345,080 dated Oct. 12, 2011, 15 pgs.
Non-Final Office Action cited in U.S. Appl. No. 12/345,080 dated Nov. 21, 2011, 18 pgs.
Reply Non-Final Office Action cited in U.S. Appl. No. 12/345,080 dated Feb. 21, 2012, 15 pgs.
Final Office Action cited in U.S. Appl. No. 12/345,080 dated Jul. 5, 2012, 23 pgs.
Reply Final Office Action cited in U.S. Appl. No. 12/345,080 dated Oct. 5, 2012, 14 pgs.
Non-Final Office Action cited in U.S. Appl. No. 12/345,080 dated Dec. 19, 2012, 18 pgs.
Reply Non-Final Office Action cited in U.S. Appl. No. 12/345,080 dated Mar. 19, 2013, 14 pgs.
Final Office Action cited in U.S. Appl. No. 12/345,080 dated Jun. 28, 2013, 17 pgs.
Reply Final Office Action cited in U.S. Appl. No. 12/345,080 dated Sep. 30, 2013, 16 pgs.
Non-Final Office Action cited in U.S. Appl. No. 12/345,080 dated Jan. 3, 2014, 18 pgs.
Reply Non-Final Office Action cited in U.S. Appl. No. 12/345,080 dated Apr. 3, 2014, 13 pgs.
Final Office Action cited in U.S. Appl. No. 12/345,080 dated May 1, 2014, 22 pgs.
Reply Final Office Action cited in U.S. Appl. No. 12/345,080 dated Aug. 13, 2014, 14 pgs.
Non-Final Office Action cited in U.S. Appl. No. 12/978,728 dated Sep. 26, 2011, 26 pgs.
Reply Non-Final Office Action cited in U.S. Appl. No. 12/978,728 dated Dec. 27, 2011, 15 pgs.
Final Office Action cited in U.S. Appl. No. 12/978,728 dated May 14, 2012, 23 pgs.
Reply Final Office Action cited in U.S. Appl. No. 12/978,728 dated Jul. 16, 2012, 12 pgs.
Notice of Allowance cited in U.S. Appl. No. 12/978,728 dated Aug. 3, 2012, 11 pgs.
EP Communication cited in EP Application No. 10793071.1 dated Apr. 11, 2014, 5 pgs.
Reply EP Communication cited in EP Application No. 10793071.1 dated 84811/2014, 13 pgs.
"Staionary digital breast tomosynthesis system with a multi-beam field emission x-ray source array", Mar. 18, 2008 Guang Yang, Ramya Rajaram, Guyohua Cao, Shabana, Sultant, Zhijun Liu, Daiv Dlalush, Jianping Lu and Otto Zhou, Medical Imaging 2008: Physics of Medical Imaging, edited by Jiang Haieh, Ehsan Samei, Proc. of SPIE vol. 69t3, (2008), 10 pgs.
Japanese Office Action cited in Japanese Application No. 2013-539801 dated May 13, 2014, 4 pgs.
International Search Report cited in related application No. PCT/US2010/056855 dated Jul. 27, 2011.
Korean Office Action cited in Japanese Application No. 2013-539801 dated Mar. 24, 2014, 3 pgs.
Int. Preliminary Report cited in PCT Application No. PCT/US2010/056855 dated May 21, 2013, 10 pgs.
EP Communication cited in EP Application No. 10 793 071.1 dated Nov. 12, 2015, 6 pgs.
EP Communication cited in EP Application No. 10 793 071.1 dated May 9, 2016, 4 pgs.
Reply EP Communication cited in EP Application No. 10 793 071.1 dated Sep. 1, 2016, 8 pgs.

* cited by examiner

MULTI-MODALITY IMAGE ACQUISITION

BACKGROUND

The present application relates to the examination of objects using different image acquisition modalities. It finds particular application to the use of ultrasound and x-rays in mammography examinations. It also relates to medical and other applications where information from multiple imaging modalities can be used to provide additional information about the structure and/or function of an object.

Radiographic imaging systems provide information, or images, of an object under examination or rather interior aspects of the object. For example, in radiographic imaging systems, the object is exposed to radiation, and one or more images are formed based upon the radiation absorbed by the object, or rather an amount of radiation that is able to pass through the object. Typically, highly dense objects absorb (e.g., attenuate) more radiation than less dense objects, and thus an object having a higher density, such as a bone or gland, for example, will appear differently than less dense objects, such as fatty tissue or skin, for example.

In medicine, radiographic imaging systems are commonly used to detect broken bones, masses, calcium deposits, etc. that are not visible to the naked eye. One type of radiographic image system is a mammography unit that generally comprises a radiation source, one or more compression paddles, and a detector array. The detector array is mounted on a diametrically opposing side of the breast tissue (e.g., the object under examination) from the radiation source and a compression paddle. The radiation source emits ionizing radiation (e.g., x-rays) that traverses the breast tissue while it is compressed. Radiation that traverses the breast tissue is detected by the detector array. In digital radiology, flat panel detectors detect the radiation, and reconstruction algorithms are used to create one or more two-dimensional (2D) images of the breast tissue in the latitudinal dimension (e.g., orthogonal to a center x-ray beam and/or substantially parallel to the detector array).

While two-dimensional, radiographic images are useful in mammography and other applications, these images provide little or no resolution in the longitudinal direction (e.g., parallel to the x-ray beam and/or orthogonal to the detector plane formed by the detectors). On a breast examination, for example, a two-dimensional, radiographic image cannot provide information about whether a mass is nearer the radiation source or the detector array. A potentially cancerous mass, for example, may be masked by a dense aspect of the object, such as a gland, if the mass is on top of the gland or vice versa, for example. Moreover, because objects of interest (e.g., cancerous cells) can share similar density information as objects that are not of interest, objects that are not of interest are sometimes mistakenly classified as an object of interest, resulting in a false positive.

Ultrasound imaging is one common, additional method used to confirm or reject an initial positive finding. Typically, an ultrasound probe transmits high-frequency ultrasound waves (e.g., pulses) into the object under examination. As the ultrasound waves travel through the object, they propagate differently through various tissues. The ultrasound waves that are reflected (e.g., echoes) are detected by the probe, and an ultrasound subsystem calculates the distance from the probe to the objects and/or the intensities of the echoes. An image of the target inside the breast is formed based upon the calculations.

While current cancer screening techniques have proven effective for detecting early signs of cancer in some situations, there remains room for improvement. The radiographic examination and ultrasound examination are typically done at different times and in different physical positions. For example, in breast cancer screening, the mammography exam is usually done with a woman standing upright and the breast tissue in a compressed state, while the ultrasound examination is done with the woman flat on her back and the breast stretched out (e.g., to reduce the distance the ultrasound waves have to travel into the breast, thereby improving the image quality). Therefore, it is difficult to compare the ultrasound images with the radiographic images and to detect similar details in the radiographic and the ultrasound images. Additionally, initial false positives can generate feelings of anxiety or distress that can last well after the ultrasound examination confirms that the initial positive finding was false.

SUMMARY

Aspects of the present application address the above matters, and others. According to one aspect, an examination apparatus is provided. The examination apparatus comprises a radiation source configured to emit radiation into an examination region of the examination apparatus and a detector array configured to detect radiation that has traversed an object under examination situated in the examination region. The examination apparatus further comprises an ultrasound frontend component configured to transmit one or more ultrasound waves into the examination region. The one or more ultrasound waves are transmitted in a direction substantially parallel to a trajectory of a center beam of radiation.

According to another aspect, an examination apparatus is provided. The examination apparatus comprises an ultrasound frontend component configured to transmit one or more ultrasound waves towards an object under examination, the object being in an orientation substantially similar to its orientation during a radiographic examination. The ultrasound frontend component is configured to emit the one or more ultrasound waves in a direction substantially parallel to a direction of a center beam of radiation.

According to yet another aspect, a method of acquiring data from two examination modalities regarding an object under examination is provided. The method comprises performing a radiographic examination on the object under examination, the object having a first orientation. The method also comprises performing an ultrasound on the object under examination while the object is in the first orientation, where one or more ultrasound waves are transmitted in a direction substantially parallel to a trajectory of a center beam of radiation.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques are provided for generating an ultrasound image(s) and a radiographic image(s) that depict a same plane of an object under examination. In this way, the sensitivity illustrated in an ultrasound image may be combined with the morphological detail illustrated in a radiographic image, for example. In one embodiment, an ultrasound subsystem comprising an ultrasound frontend component (e.g., one or more steerable transducers) are coupled to a radiographic examination apparatus (e.g., a mammography system) that substantially immobilizes the object. While the object is immobilized, radiation and ultrasound waves may traverse the object in substantially the same direction, for example. That is, by immobilizing the object, an orientation of the object may remain substantially constant during both the radiographic examination and the ultrasound examination, for example.

It is to be appreciated that an orientation or rather a fixed orientation or the like as used herein generally means that the object or rather aspects therein (e.g., anatomical structures, tumors, glands, fatty deposits, etc.) have a substantially same geometric positioning within the object or remain substantially fixed relative to one another during both the radiographic and ultrasound examinations. That is, the object (e.g., breast tissue) is not moved between the different examinations and/or during any portion of any one of the examinations (e.g., it continues to remain compressed between compression paddles during both examinations and is not uncompressed between or during either of the examinations). In this manner, an area of interest (e.g., potential tumor) that may be discovered during a radiographic examination, for example, remains in a same location during an ultrasound examination so that the area of interest can be examined in greater detail. Nevertheless, while the orientation of the object may remain substantially constant relative to itself, for example, surrounding components may, of course, move relative to the "fixed" object. For example, a radiation source, detector array, transducers, etc. may move in and/or around the object so that data may be acquired.

Figure 1:
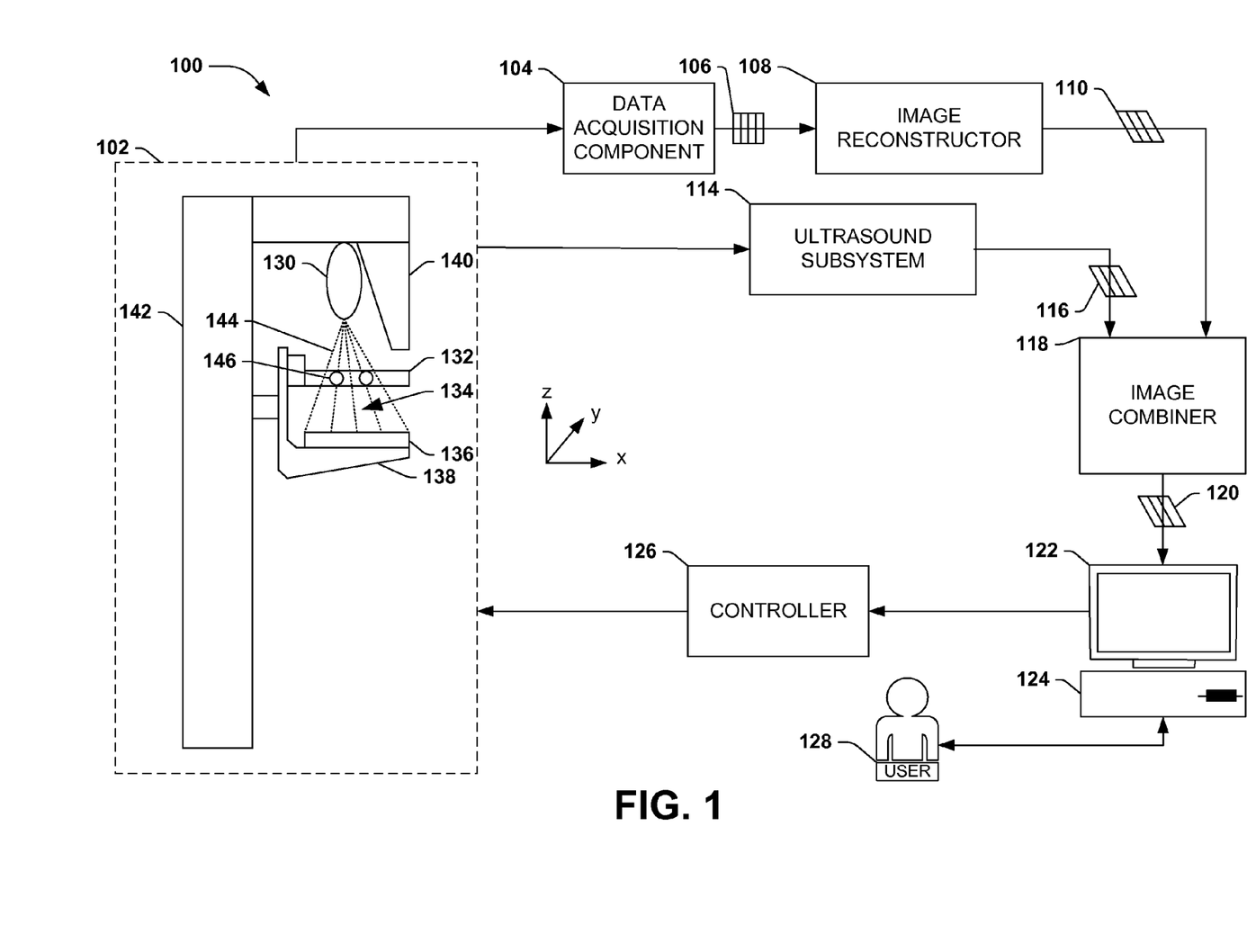
FIG. 1 is a schematic block diagram illustrating an examination apparatus wherein radiographic and ultrasound information may be acquired.

FIG. 1 is an illustration of an example environment 100 of an example examination system in which one or more ultrasound images and one or more radiographic images may be generated. Such an examination system may be used to detect a tumor at a medical center, for example. For example, in one embodiment, the examination system is a mammography scanner configured to examine breast tissue for potential signs of breast cancer.

As illustrated, the examination apparatus typically comprises an object examination apparatus 102 configured to examination an object (e.g., human tissue). One or more images of the examined object may be presented on a monitor 122 of a workstation 124 for viewing by a human user 128. In this way, targets of an object under examination that are not visible to the naked eye (e.g., cancer tumors comprised within breast tissue) may be displayed in the one or more images and, ultimately, may be detected by the human user 128. It will be appreciated that while the examination apparatus described herein is configured similar to a mammography examination system, the instant application is not intended to be so limited. That is, to the extent possible, the instant application, including the scope of the claimed subject matter, is intended to be applicable to other systems as well. It will also be appreciated that the example environment 100 merely illustrates an example schematic and is not intended to be interpreted in a limiting manner, such as necessarily specifying the orientation of the components described herein. For example, a data acquisition component 104 as illustrated in FIG. 1 may be part of the object examination apparatus 102, or more particular may be part of a detector array 138 of the object examination apparatus 102.

In the example environment 100, the object examination apparatus 102 is configured to examine an object under examination and transmit data related to the examination to other components of the examination system. The object examination apparatus 102 comprises a radiation source 130 (e.g., such as an ionizing radiation source and/or an x-ray source) and a detector array 138. During an examination of the object situated in an examination region 134 of the object examination apparatus 102, the radiation source 130 emits fan, cone, wedge, and/or other shaped radiation 144 configurations into the examination region 134. It will be appreciated that additional features of the radiation source 130 may be discussed with respect to FIGS. 2-3.

Different aspects or parts of the object may attenuate radiation 144 that traverses the object under examination (e.g., the object situated in the examination region 134) differently, and a radiographic image(s) may be generated based upon the attenuation, or rather (indirectly based on) the variations in the number of radiation photons that are detected by the detector array 138. For example, more dense aspects of the object(s) may attenuate more of the radiation 144 (e.g., causing fewer photons to strike the detector array 138) than less dense materials, such as skin or healthy fat tissue.

In one embodiment, the object examination apparatus 102 further comprises an immobilization device that is configured to immobilize the object under examination. For example, where the examination system is a mammography scanner as illustrated in the example environment 100, the immobilization device may comprise a top compression paddle 132 and a bottom compression paddle 136 configured to immobilize the breast tissue. The examination region 134 is situated between the top compression paddle 132 and the bottom compression paddle 136. When the object (e.g., breast tissue) is inserted between the top and bottom compression paddles 132, 136, the object is compressed (e.g., to even out the tissue and substantially immobilize the breast). While the object is under compression, radiation 144 may be emitted from the radiation source 130. Radiation 144 that traverses the breast while it is compressed is detected by the detector array 138 that is located within and/or below the bottom compression paddle 136. It will be appreciated that while the illustrated immobilization device comprises two compression paddles 132, 136, in another embodiment, the immobilization device merely comprises a single compression paddle 132 and the bottom portion of the breast tissue is supported and/or immobilized merely by the detector array 138, for example. In other embodiments, there may be multiple compression paddles in any suitable arrangement.

A vertical support stand 142 may provide a means for suspending the compression paddles 132 and 136, the radiation source 130, and/or the detector array 138 above the ground. For example, the vertical support may be several feet tall and the compression paddles 132 and 136 may be adjustable along the vertical support 142 (e.g., in a z direction) to adjust for the varying heights of humans, for example. A shield 140 may protect a person's head from exposure to the radiation 144.

The object examination apparatus 102 may also comprise an ultrasound frontend component 146. The ultrasound frontend component 146 may be configured to transmit a plurality of ultrasound waves into the examination region 134 and/or detect reflected ultrasound waves, for example, that have interacted with the object, in such a manner that the detected ultrasounds waves can be used to generate an ultrasound image of object that depicts a plane within the object substantially parallel to a plane depicted in an x-ray image of the object. For example, in mammography, a horizontal slice of breast tissue is depicted in a radiographic image, and the ultrasound frontend component 146 may be configured to transmit and/or receive ultrasound waves in such a manner that it ultimately causes the resulting ultrasound image(s) to also depict a horizontal slice of breast tissue in a plane substantially parallel to the plane of the radiographic image. In one example, the ultrasound frontend component 146 transmits ultrasound waves in a direction substantially parallel to a trajectory of a center beam of radiation associated with the radiation source 130 and/or perpendicular to a detector surface of the detector array 138 that detects radiation. It will be understood to those skilled in the art that the terms "center beam of radiation" as used herein refers to a beam of radiation that impacts the detector array 138 at a substantially ninety degree angle (e.g., the center beam of a fan, cone, wedge, or other shaped radiation configuration). Stated differently, a center beam of radiation is a beam of radiation that is emitted from a radiation source 130 positioned directly above the detector array, such that in both an x direction and a y direction the beam of radiation impinges the detector array at a substantially ninety degree angle (e.g., where the detector array 138 is substantially flat). It will be appreciated that in one embodiment, the detector array 138 may be curved (e.g., as opposed to flat) and/or radiation may not be emitted from a radiation source 130 positioned directly above the detector array 138, and thus no such center beam of radiation may exists. In such an instance, a center beam would be an imaginary beam of radiation emitted from an imaginary source positioned directly above the detector array 138.

It will be appreciated that the ultrasound frontend component 146 may be configured to detect transmission waves and/or reflection waves depending upon its configuration. In one example, a single transducer of the ultrasound frontend component 146 both transmits ultrasound waves and detects those ultrasound waves that have reflected off targets in the object. In another example, one transducer transmits ultrasound waves and another transducer, positioned adjacent to the one transducer or on a diametrically opposing side of the object, detects ultrasound waves that have traversed the object under examination. It will be appreciated, however, that any suitable number of transducers and/or transducer arrangements may be implemented.

It will also be appreciated that the ultrasound frontend component 146 and/or components of the ultrasound frontend component 146 (e.g., one or more transducers comprised within the ultrasound frontend component 146) may be configured to adjust vertically relative to the object (e.g., to move in a z direction) and/or to tilt within the horizontal plane (e.g., in x and/or y directions)) and/or a focal plane of the ultrasound frontend component may be adjusted (e.g., vertically in the z direction) within the object to acquire data that may used to create a plurality of images, respective images depicting various parallel planes of the object. In this way, a plurality of ultrasound images may be formed, respective ultrasound images of the plurality depicting a plane of the object that is substantially parallel to the planes depicted in the other ultrasound images and substantially parallel to planes depicted in one or more radiographic images. In one example, a doctor may compare a series of ultrasound images, each depicting a unique plane, or slice, of the object, for example, with a respective radiographic image(s) depicting a similar or same plane of the object.

In the example environment 100, a data acquisition component 104 is operably coupled to the object examination apparatus 102 and is configured to collect information and data related to radiation that was detected by the detector array 138. For example, in one embodiment, the data acquisition component 104 is configured to receive analog signals generated by the detector array 138, which are indicative of detected radiation, and to convert the analog signals into the digital domain using analog-to-digital techniques known to those skilled in the art. Moreover, the data acquisition component 104 may be configured to compile the digital data (e.g., yielded from a plurality of pixels of the detector array 138) into one or more projection images 106, where respective projection images 106 are indicative of a horizontal plane, or horizontal slice, within the object, for example.

The example environment 100 also comprises an image reconstructor 108 configured to receive the one or more projection images 106 from the data acquisition component 104 and generate one or more two-dimensional (2D), radiographic images 110 that are more understandable by a user 128 viewing the radiographic image(s) 110. Stated differently, the image reconstructor 108 is configured to convert the images 106 from projection space to image space using suitable analytical, iterative, and/or other image reconstruction techniques known to those skilled in the art (e.g., 2D filtered backprojection, tomosynthesis reconstruction, etc.). It will be appreciated that, like the projection image 106 from which a two-dimensional image 110 is yielded, respective two-dimensional, radiographic images 110 depict horizontal planes, or horizontal slices, within the object. Stated differently, the radiographic image(s) 110 illustrate the latitudinal dimension (e.g., orthogonal to a center x-ray beam and parallel to the detector array) of the object. That is, the images may not depict the vertical height, for example, of a target inside an object when radiation 144 is emitted from above the object under examination. Thus, for example, where merely one image 110 is generated from an examination of the object, the plane depicted in the radiographic image 110 may represent the entire volume of the object (e.g., entirety of compressed breast).

Where two or more images 110 are generated from the examination of the object, respective planes may depict different sections along the vertical height of the object, for example. Thus, for example, a first radiographic image may depict a first horizontal plane (e.g., where the vertical dimension of aspects of the object within the object slice represented by the plane is collapsed) and a second radiographic image may depict a second horizontal plane, that is different from the first horizontal plane. It will be appreciated that while reference is made to images respectively depicting a different slice, one or more images may represent a same slice of the object. For example, first and second radiographic images may depict a same horizontal plane within the object. Moreover, first and second are generally used herein merely as designations of items, but do not necessarily indicate an ordering. For example, a first image does not have to be acquired (e.g., temporally) before a second image.

The example environment 100 of the examination system also comprises an ultrasound subsystem 114 that is operably coupled to the object scanning apparatus 102, or more particularly the ultrasound frontend component 146 and is configured to collect information and/or to transmit ultrasound waves that are detected by the ultrasound frontend component 146. The ultrasound subsystem 114 may also be configured to reconstruct the collected information into image space data 116. As an example, data from a plurality of transducers positioned above the object (e.g., and transmitting ultrasound waves towards the detector array 138) may be compiled to generate two-dimensional ultrasound image(s) 116 using techniques known to those skilled in the art (e.g., beam forming techniques). It will be understood to those skilled in the art that the one or more two-dimensional, radiographic images 110 and the one or more ultrasound images 116 depict substantially parallel planes of the object under examination.

In some instances, the radiographic images 110 and the ultrasound images 116 may be spatially coincident to one another. That is, the plane of the object depicted in at least one radiographic image may correspond to a plane of the object depicted in at least one ultrasound image, in such a way that the ultrasound image may be overlaid onto the radiographic image or vice-versa. For example, if the radiographic images 110 depict twenty different planes of object (e.g., each plane representing a horizontal slice 1/20 the height of the total object), the ultrasound subsystem 114, for example, may be configured to adjust a focal plane, or focus, of the ultrasound waves, so as to cause twenty ultrasound images 116 to be produced. A first of the twenty ultrasound images 116 that is produced by the ultrasound subsystem 114 may have spatial coincidence with a first of the radiographic images 110, a second with a second, a third with a third, etc., for example.

In the example environment 100, the examination apparatus further comprises an image combiner 118 that is in operable communication with the ultrasound subsystem 114 and the image reconstructor 108. The image combiner 118 is configured to combine one or more radiographic images 110 with one or more ultrasound images 116 to form one or more combined images 120 (e.g., through the process of fusion) when the radiographic image(s) and the ultrasound image(s) are spatially coincident. That is, the image combiner 118 is configured to combine complementary information from two modalities (e.g., a radiographic image 110 and an ultrasound image 116) through suitable analytical techniques (e.g., retrospective registration algorithms, algorithms based on entropy, etc.).

The example environment 100 also includes a workstation 124 (e.g., a computer) configured to receive the combined image(s) 120, which can be displayed on the monitor 122 to the user 128 (e.g., medical personnel). In this way, a user 128 can inspect the image(s) to identify areas of interest within the object. The terminal 124 can also be configured to receive user input which can direct operations of the object examination apparatus 102 and/or can direct the monitor 122 to display a combined image 120 illustrating a particular object slice, for example.

In the example environment 100, a controller 126 is operably coupled to the terminal 124. In one example, the controller 126 is configured to receive user input from the terminal 124 and generate instructions for the object examination apparatus 102 indicative of operations to be performed.

It will be understood to those skilled in the art that other configurations and components for an examination system are also contemplated. For example, in one embodiment, the examination system does not comprise an image combiner 118. Thus, the radiographic image and the ultrasound image are individually displayed on the monitor 122, and the user 128 can visually compare the images from the multiple modalities, for example. As another example, the data acquisition component 104 may be part of the object examination apparatus 102.

Figure 2:
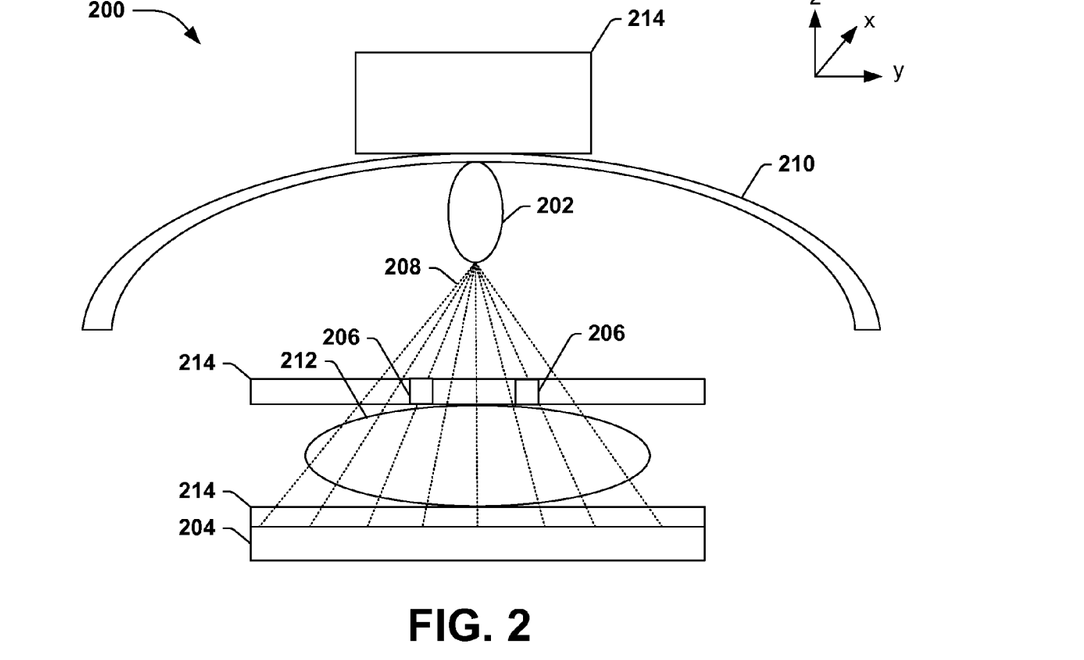
FIG. 2 illustrates a cross-sectional area of an object scanning apparatus while radiation is being emitted from a radiation source.

FIG. 2 is a cross-sectional area of an example object examination apparatus 200 (e.g., 102 in FIG. 1) that illustrates radiation 208 being emitted from a radiation source 202 (e.g., 130 in FIG. 1). The object examination apparatus 200 comprises a radiation source 202, a detector array 204 (e.g., 138 in FIG. 1), and openings 206 through which a portion of an ultrasound frontend component (e.g., 146 in FIG. 1) may be inserted. As will be described further with respect to FIGS. 3 and 6, it will be appreciated that during a radiographic examination (e.g., during the emission of radiation 208), the ultrasound frontend component is removed, and thus the openings 206 may be empty, so that the ultrasound frontend component does not interfere with the radiographic examination (e.g., so that the ultrasound frontend component does not attenuate radiation 208), for example.

To generate a plurality of radiographic images respectively depicting different planes of an object 212 under examination, radiation is generally emitted from a plurality of directions relative to the object 212. Stated differently, the object is viewed from a multitude of perspectives. The data from the variety of perspectives may be combined or synthesized by an image reconstructor (e.g., 108 in FIG. 1) using known digital image processing and/or filtering techniques (e.g., tomosynthesis). Respective images may be selected to be a horizontal plane (e.g., a horizontal slice) within the object, which is parallel to a detector surface of the detector array 204 (e.g., a surface upon which radiation impinges), and depicts aspects of the object within a particular range in the z-dimension, for example. In this way, a substantially three-dimensional image of the object under examination may be formed by stacking two-dimensional images.

In the illustrated example object examination apparatus 200, the object is viewed from a multitude of perspectives by rotating (e.g., 20 degrees left and/or right of center) the radiation source 202 (e.g., in a y, z plane) relative to the object 212 under examination using a guide mechanism 210.

That is, the object is immobilized such that it remains stationary and the radiation source 202 rotates about the object. The guide mechanism 210 may be suspended from a vertical support stand 214 (e.g., 142 in FIG. 1).

It will be understood to those skilled in the art that the guide mechanism 210 may be unnecessary in certain applications, such as those in which data is not collected from a variety of perspectives, the radiation source 202 is stationary while the detector array 204 rotates, etc. For example, where the radiographic examination is intended to merely yield radiographic images depicting a single plane of the object 212 (e.g., the vertical dimension of the object 212 is collapsed into a single plane), radiation may be emitted from a single direction, and thus a guide mechanism 210 may be unnecessary.

It will be appreciated that rotating the radiation source 202 is merely one example technique for emitting radiation from different directions relative to the object 212 under examination. For example, in another embodiment, the radiation source 202 comprises a plurality of nano-tube field emitting cathodes positioned about the object 212 under examination. In this way, radiation 208 may be emitted from a plurality of directions relative to the object 212 without moving the radiation source 202 by merely selectively activating the different cathodes, for example.

Radiation 208 that traverses the object 212 is detected by the detector array 204 positioned on a diametrically opposing side of the object 212 relative the radiation source 202. In the illustrated example, the object 212 (e.g., tissue) is compressed between an immobilization device 214 (e.g., top and bottom compression paddles similar to those used on mammography apparatuses) to compress and/or even out the object 212 (e.g., to promote tissue spreading). As will be discussed in more detail with respect to FIG. 5, the immobilization device 214 may comprise openings 206 through which a portion(s) of the ultrasound frontend component may be inserted if a portion of the immobilization device 214 would otherwise interfere with the ultrasound frontend component (e.g., if ultrasound waves would be reflected by the immobilization device 214). For example, as illustrated, a portion of a top compression paddle of the immobilization device 214 comprises notches, or openings 206, that allow a portion of the ultrasound frontend component to be lowered into place, such that it makes contact with the object 212 under examination.

It will be appreciated that FIG. 2 merely illustrates one example of an object examination apparatus 200 and is not intended to limit the scope of the claims. For example, in another embodiment, the immobilization device 214 is comprised of a material that does not interfere with ultrasound waves, and thus the immobilization device does not comprise any openings 206 (e.g., the ultrasound frontend component is merely rested on top of the immobilization device). In another embodiment, one or more openings 206 may be comprised in a bottom portion of the immobilization device 214 (e.g., in a bottom compression paddle). In this way, a portion of the ultrasound frontend component may be inserted below the object 212 under examination. That is, portions of the ultrasound frontend component may be positioned above the object 212, or below the object 212, or both above and below the object 212, for example.

Figure 3:
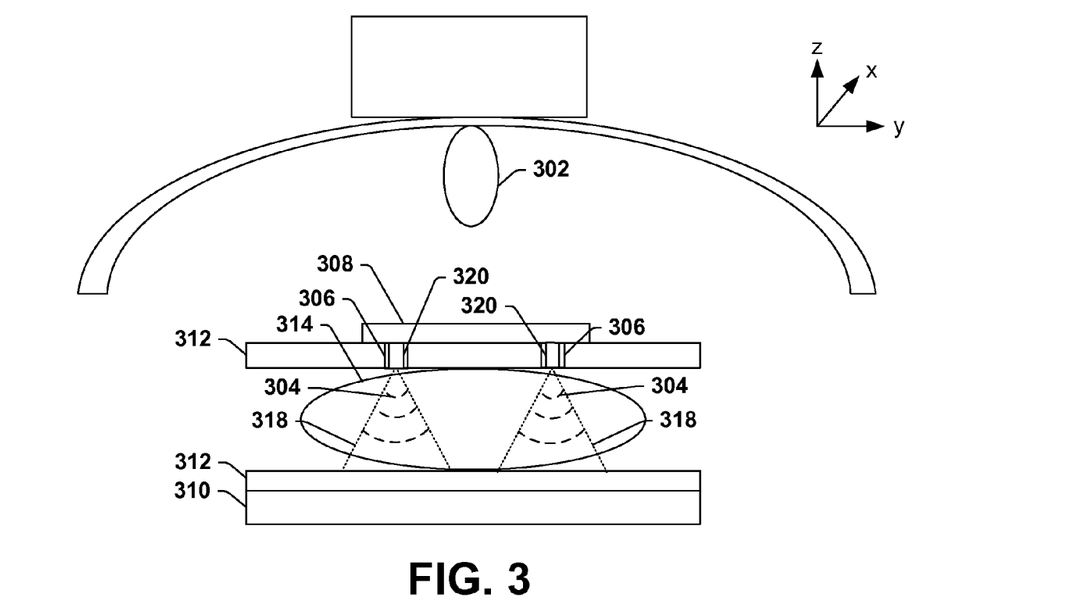
FIG. 3 illustrates a cross-sectional area of an object scanning apparatus while ultrasound waves are being transmitted from an ultrasound frontend component.

FIG. 3 is a cross-sectional area of an example object examination apparatus 300 (e.g., 102 in FIG. 1) that illustrates the object examination apparatus 300 when no radiation is being emitted from a radiation source 302 (e.g., 130 in FIG. 1). It will be appreciated the FIG. 3 is substantially similar to FIG. 2 except that radiation (e.g., 208 in FIG. 2) is not being emitted, and ultrasound waves 304 are being transmitted.

As illustrated, during a time when no radiation is being emitted (e.g., before a radiographic examination begins and/or after a radiographic examination ends), a portion of the ultrasound frontend component 308 (e.g., steerable transducers 320 of the ultrasound frontend component 308) is inserted into the openings 306 (e.g., 206 in FIG. 2) by an ultrasound positioning system (not illustrated). The ultrasound frontend component 308 is configured to transmit and/or receive ultrasound waves 304 in a direction substantially parallel to a trajectory of a center beam of radiation. Stated differently, as illustrated, the ultrasounds waves 304 move in substantially the same direction as radiation (e.g., 208 in FIG. 2). Thus, the direction of travel for the ultrasound waves 304 is substantially perpendicular to a plane formed by a detection surface of the detector array 310 (e.g. 204 in FIG. 2).

It will be appreciated that in one embodiment, as illustrated, an immobilization device 312 (e.g., 214 in FIG. 2), such as compression paddles, for example, are configured to continue to immobilize the device during the ultrasound examination. That is, the immobilization device 312 is configured to immobilize the object 314 (e.g., 212 in FIG. 2) during both the radiographic examination and the ultrasound examination. In this way, the object 314 under examination remains in a substantially similar orientation during the emission of the radiation and during the transmission of one or more ultrasound waves. It will be appreciated that where the object 314 may remain in a substantially similar orientation during both the radiographic and ultrasound examinations without the assistance of an immobilization device 312, such a device 312 may not be used.

As illustrated, a trajectory 320 of the ultrasound waves 304 diverges as the ultrasound waves 318 move further away from the ultrasound frontend component 308 (e.g., the area traversed by the ultrasound waves 304 increases as the ultrasound waves become more distance from their respective source). Generally, it is desirable that the entire object 314 under examination be traversed by ultrasound waves 304. Thus, portions of the ultrasound frontend component 308 (e.g. transducers 320 of the ultrasound component) may be configured to move to cause ultrasound waves 304 to be transmitted in different directions. For example, in one embodiment, the ultrasound frontend component 308 comprises steerable transducers that may be steered (e.g., left and right and/or tilted) such that ultrasound waves 304 are transmitted in such a way that ultrasound waves 304 traverse the entire area of the object 314. Moreover, it will be appreciated that while the example object examination apparatus 300 comprises two transducers 320 configured to transmit ultrasound waves, more or fewer transducers may be used depending upon the application (e.g., the horizontal length of the object 314, the trajectory 318 of the ultrasound waves, etc.).

As the ultrasound waves 304 move through the object 314, some aspects of the object reflect the ultrasound waves 304. Such reflected waves may be detected by the ultrasound frontend component 308 (e.g., the same transducer that transmitted the wave or a different transducer) to generate ultrasound projection data. Moreover, in another embodiment, the ultrasound frontend component may comprise additional detection transducers on an opposite side of the object 314 relative to emission transducers. In this way, ultrasound waves 304 that pass through the object 314 (e.g., and are not reflected) may be detected.

It will be appreciated to those skilled in the art that by varying the focusing of the ultrasound transmission, or by varying a focal plane of the ultrasound, one or more ultrasound images (e.g., 116 in FIG. 1) may be generated (e.g., by an ultrasound subsystem 114 in FIG. 1) using a suitable analytical, iterative, and/or other reconstruction technique (e.g., similar to the techniques used to generate computed tomography images from x-ray data). Respective ultrasound images can be processed to depict a horizontal plane, or horizontal slice, within the object and, in one example, the images emphasize one or more particular characteristics of detected tissues (e.g., elastography, reflection, transmission, etc.).

Thus, returning to FIG. 2, by emitting radiation from a plurality of directions relative to the object 212, radiographic images (e.g., 110 in FIG. 1) may be produced respectively depicting different horizontal planes, or horizontal slices within the object 212. Returning to FIG. 3, by transmitting ultrasound waves 304 in a direction substantially parallel to a direction radiation travels and by varying the focus within projection data generated from the detected ultrasound waves 304, ultrasound images (e.g., 116 in FIG. 1) may be produced respectively depicting different horizontal planes, or slices of the object 314. It will be appreciated that in one embodiment, one or more of the radiographic images may be substantially spatially coincident to one or more ultrasound images and, in one embodiment, may be combined (e.g., to form an image having the sensitivity of an ultrasound image and the morphological details of a radiographic image).

It will be appreciated that while reference is made to producing radiographic images and ultrasound images depicting different horizontal planes, a plurality of images may be produced depicting the same plane. For example, two or more radiographic images may depict substantially the same horizontal plane and/or two or more ultrasound images may depict substantially the same horizontal plane within the object, and one or more of the radiographic images may be combined with one or more of the ultrasound images (e.g., for enhanced resolution).

Figure 4:
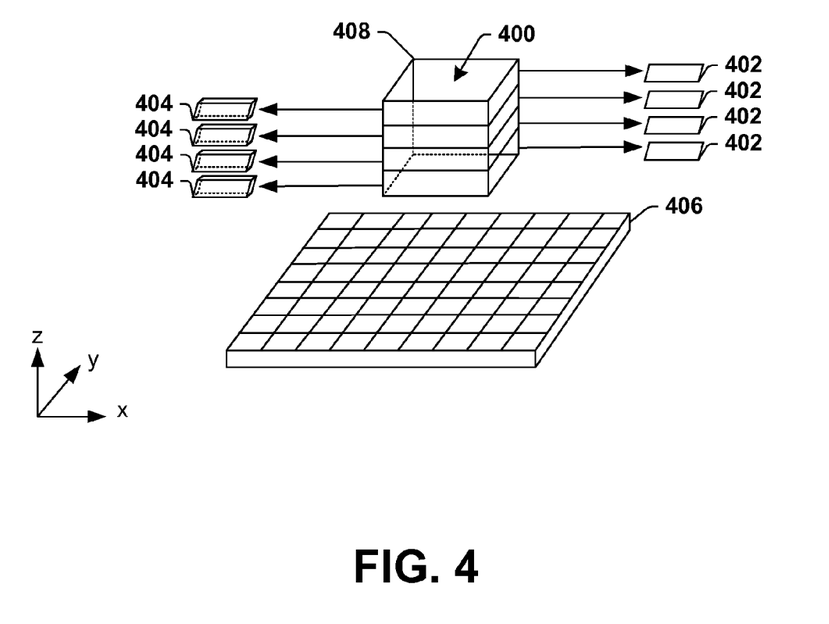
FIG. 4 illustrates example planes of an object that may be depicted in radiographic images and/or ultrasound images.

FIG. 4 illustrates example horizontal slices 400 (e.g., examination planes) of an object 408 (e.g., 314 in FIG. 3) that undergoes both a radiographic examination and an ultrasound examination while maintaining a substantially fixed orientation. As discussed with respect to FIG. 2, the radiographic images generally depict one or more horizontal slices 400 of the object (e.g., where the z dimension of the object represented by the slice is flattened) that are substantially parallel to a detector array 406 (e.g., 138 in FIG. 1). For example, if the object is merely divided into a single slice and the radiographic image 402 represents the entire slice, the entire z dimension of the object 408 is represented by the single radiographic image (e.g., there is no discernable z coordinate in the radiographic image). However, as illustrated, when radiographic data is acquired at a plurality of perspectives (e.g., radiation is emitted from a plurality of directions relative to the object 408) and combined (e.g., using tomosynthesis techniques), radiographic images 402 depicting the illustrated example horizontal slices 400 may be produced from the detected radiation, where respective images 402 represent a different portion of the z dimension (e.g., as illustrated, the z dimension is dissected into four parts).

Ultrasound images 404 depicting similar horizontal planes 400 to those depicted in the radiographic images 402 may also be produced (e.g., the ultrasound images depict planes within the object 408 that are substantially parallel with the detector array 406). For example, the ultrasound images 404 may depict the horizontal planes 400 in a flattened state (e.g., where there is no discernable z dimension) or in an unflattened state (e.g., depicting x, y, and z dimensions). The example ultrasound images 404 depict the examination planes in an unflattened state. That is, they are depicted as having x, y and z dimensions. It will be appreciated that unflattened ultrasound images may be useful to more easily determine the z coordinate of an area of interest within the object, for example.

Once radiographic images 402 and ultrasound images 404 are acquired, radiographic and ultrasound images that are spatially coincident may be combined (e.g., by an image combiner similar to 118 in FIG. 1) to form a combined image (e.g., 120 in FIG. 1) that depicts that sensitivity of the ultrasound image and/or the morphological detail of the radiographic image, for example. That is, a radiographic image 402 depicting a particular plane within the object may be combined with an ultrasound image 404 depicting a similar plane to form a combined image.

It will be appreciated that while the images may be combined to form combined images, the ultrasound images 404 and the radiographic images 402 may also or instead remain separated and viewed independently (e.g., manually by a physician), for example. It will also be appreciated that at least some of the ultrasound images 404 and the radiographic images 402 may not be spatially coincident (e.g., because they depict different planes within the object 408). Nevertheless, they may provide helpful (e.g., diagnostic) information, such as the location of a mass/tumor in the x, y and z direction, for example.

Figure 5:
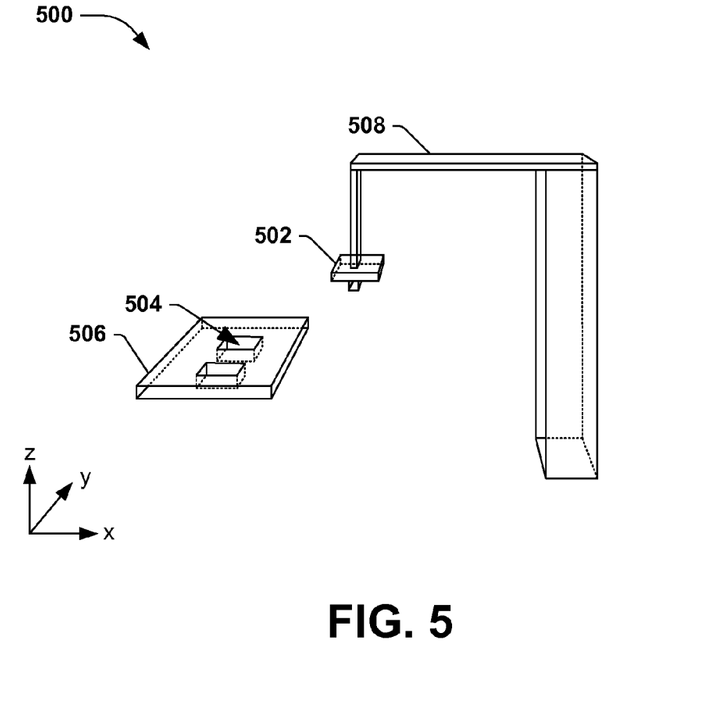
FIG. 5 illustrates an example ultrasound frontend component, example ultrasound positioning system, and an example immobilization device.

FIG. 5 illustrates an example environment 500 for positioning an ultrasound frontend component 502 (e.g., 308 in FIG. 3) in an opening(s) 504 (e.g., 306 in FIG. 3) of an immobilization component 506 (e.g., 312 in FIG. 3), such as in a precision cut opening of a compression paddle of a mammography scanner, for example. In this way, an ultrasound frontend component 502 can be positioned near the object (e.g., 314 in FIG. 3) when a radiographic examination is not being performed and can be removed while the radiographic examination is being performed. Stated different, as discussed above, the ultrasound frontend component 502, if positioned in the opening during the radiographic examination, may interfere with the radiation (e.g., it may attenuate a portion of the radiation) causing artifacts, or contamination, to the radiographic image(s). To avoid this, the ultrasound frontend component 502 may be positioned in the opening(s) 504 and perform an ultrasound examination before the radiographic examination and/or after the radiographic examination. During the radiographic examination, the ultrasound frontend component 502 may be removed from the opening(s) 504 by an ultrasound positioning system 508, for example.

As illustrated, the example environment 500 comprises an ultrasound positioning apparatus 508 configured to position the ultrasound frontend component 502 at one or more locations (e.g., openings 504) during a time in which the radiographic examination is not being performed. In one embodiment, the ultrasound positioning apparatus 508 is a mechanical arm (e.g. robotic arm) that may be attached to an object examination apparatus (e.g. 102 in FIG. 1), for example. It another embodiment, the ultrasound positioning apparatus is a mechanical arm that is part of a standalone device that may be maneuvered into place by a human user, for example.

It will be appreciated that while reference is made herein to an ultrasound positioning apparatus 508, in one embodiment, the ultrasound frontend component 502 is merely positioned by a human user. That is, while using an ultrasound positioning apparatus 508 may provide some benefits (e.g., it may be able to position the ultrasound frontend component 502 in the opening(s) 504 faster, more delicately, more precisely, etc.), an ultrasound positioning apparatus, such as the ultrasound positioning apparatus 508 illustrated herein, is not required. A human user can merely insert the ultrasound frontend component 502 into the one or more openings 504 in the immobilization component 506.

Moreover, while the immobilization component 506 is illustrated as having two square openings 504, it will be appreciated to those skilled in the art that the number of openings 504 and/or the shape the openings 504 may be a function of the application and/or the type of ultrasound frontend component 502 used (e.g., the shape of transducers used, scanning angles of the ultrasound waves, etc.), and that the instant disclosure is not to be limited to the illustrated two square openings. For example, fewer transducers (and thus fewer openings) may be used where the ultrasound frontend component 502 comprises one or more tranducers configured to transmit ultrasound waves in a 160 degree arc relative to where the ultrasound frontend component 502 comprises one or more transducers configured to transmit ultrasound waves in a 50 degree arc.

Figure 6:
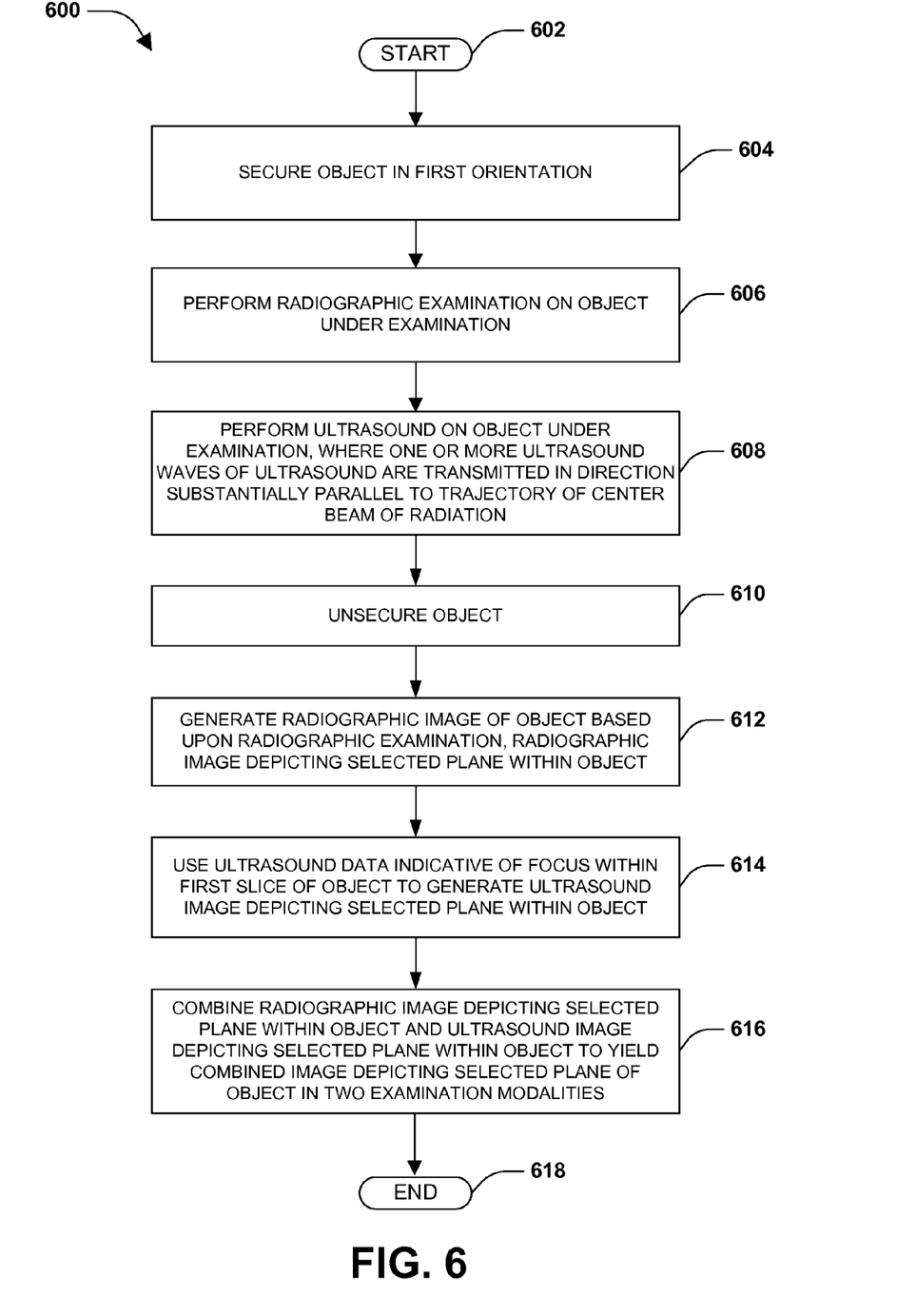
FIG. 6 is a flow diagram illustrating an example method of acquiring data from two examination modalities.

FIG. 6 illustrates an exemplary method 600 of acquiring data from two examination modalities regarding an object under examination. Such an example method 600 may be used to perform a diagnostic mammography examination on a human patient, for example.

The method begins at 602, and the object under examination is secured in a first orientation at 604. Generally, the object is secured (e.g., immobilized) to mitigate movement by the object (e.g., so that the object remains in substantially the same orientation through the examination). Moreover, where a mammography examination is being performed, securing the object may cause the object to be compressed such that the x and y dimensions of the object are expanded and the z dimension is reduced (e.g., to generate a better radiographic image). For example, in one embodiment, the object is secured using one or more compression paddles that are situated above and/or below an examination region where the object under examination resides during the examination.

It will be appreciated that if a mechanism that is securing the object, such as a compression paddle, for example, interferes with the placement and/or use of an ultrasound apparatus, the mechanism may be altered such that it does not interfere. For example, an opening(s) may be carved into the mechanism that allows a portion of the ultrasound frontend component (e.g., a transducer) to come into contact with the object under examination. In another example, the mechanism may be made of a material that does not interfere with ultrasound waves, and the ultrasound frontend component can merely be in contact with the securing mechanism (e.g., and not necessarily the object under examination).

In the example method 600, a radiographic examination is performed on the object under examination at 606. Stated differently, radiation (e.g., x-rays) is emitted from one or more directions relative to the object, traverses the object under examination (e.g., situated in the examination region), and is detected by a detector array positioned opposite the radiation source relative to the object. It will be appreciated that in one embodiment (e.g., in an application where it is preferable to generate a plurality of images representing different planes within the object), radiation is emitted from a plurality of directions relative to the object under examination so that the object is viewed from a plurality of perspectives. Numerous techniques for emitting radiation from a plurality of directions are known to those skilled in the art and are contemplated herein. For example, in one embodiment, a radiation source is rotated relative to the object, causing radiation to be emitted from a plurality of directions. In another embodiment, the radiation source comprises a plurality of nano-tube field emitting cathodes positioned in different positions relative to the object under examination, respective tubes configured to emit radiation.

It will be appreciated that while reference is made herein to a radiation source emitting radiation from a plurality of directions (e.g., to view the object from a plurality of perspectives), in another embodiment, the radiation is merely emitted from one location (e.g., the radiation source is stationary), and the object is viewed from a plurality of perspectives by rotating the object and/or by rotating the detector array. In this way, the object can be viewed from a plurality of perspectives without emitting radiation from a plurality of directions relative to the object, for example.

Radiation that is detected by the detector array generates signals that may be collected and/or compiled to generate radiographic projection data representing the object from one or more perspectives (e.g., depending upon whether the object is viewed from one or more than one perspective).

In the example method 600, an ultrasound is performed on the object under examination at 608. During the ultrasound examination one or more ultrasound waves are transmitted in a direction substantially parallel to a trajectory of a center beam of radiation. It will be understood to those skilled in the art that the terms "center beam of radiation" as used herein refers to a beam of radiation that impacts the detector array at a substantially ninety degree angle (e.g., the center beam of a fan, cone, wedge, or other shaped radiation configuration). Stated differently, a center beam of radiation is a beam of radiation that is emitted from a radiation source positioned directly above the detector array, such that in both an x direction and a y direction the beam of radiation impinges the detector array at a substantially ninety degree angle (e.g., where the detector array is flat). It will be appreciated that in one embodiment, the detector array may be curved (e.g., as opposed to flat) and/or radiation may not be emitted from a radiation source positioned directly above the detector array, and thus no such center beam of radiation exists. In such an instance, a center beam would be an imaginary beam of radiation emitted from an imaginary source positioned directly above the detector array.

Thus, in one embodiment, the ultrasound waves follow a similar trajectory to the radiation emitted by the radiation source (e.g., in FIG. 1, both the radiation and the ultrasound waves move from top to bottom). It will be appreciated that in another embodiment, the ultrasound waves may move in a trajectory substantially opposite the radiation and would still be considered to have followed a trajectory parallel to a center beam of radiation. For example, the ultrasound waves may move from the bottom to the top in FIG. 1 and the radiation may move from top to bottom or vice versa.

During the ultrasound examination, ultrasound waves are transmitted (e.g., by transducers positioned above and/or below the object (e.g., in the path of radiation if radiation were being emitted)) into the examination region while the object remains substantially in the first orientation. Ultrasound waves that bounce off targets within the object, or are reflected by portions of the object, are detected, and projection data indicative of the detected ultrasound waves may be generated. It will be appreciated to those skilled in the art that the ultrasound waves may be detected by the same components that transmit the ultrasound waves and/or may be detected by different components (e.g., different transducers may be configured to transmit and detect ultrasound waves or the same transducers may fulfill both roles).

It will be appreciated that the ultrasound and the radiographic examination generally cannot be performed at the same time because ultrasound equipment may interfere with the radiographic examination. Thus, the ultrasound examination is performed during a time in which the radiographic examination is not being performed. In the example method 600, the ultrasound examination is performed after the radiographic examination has been completed. In another embodiment, the ultrasound examination may be performed before the radiographic examination begins. Thus, the example method 600 merely illustrates one order of events, but other orders of events are contemplated herein.

Moreover, it will be appreciated that in one embodiment, where the ultrasound equipment does not interfere with the radiographic examination and the radiographic examination does not interfere with the ultrasound examination, the radiographic examination and the ultrasound examination may be performed concurrently. That is, radiation and ultrasound waves may be emitted substantially simultaneously into the same space (e.g., in the same portion of the object).

In the example method 600, the object under examination is unsecured at 610. That is, the object is permitted to change orientations after the radiographic examination and the ultrasound examination are completed. Stated differently, during the radiographic and ultrasound examinations, the object is kept in substantially the same orientation (e.g., same geometric positioning). Once both of these examinations are completed, the object is unsecured and may change orientations.

In the example method 600, one or more radiographic images of the object under examination are generated based upon information acquired from the radiographic examination, or rather based upon information acquired from the object's exposure to radiation at 612. At least one radiographic image depicts a selected plane within the object.

The radiographic images are generated using techniques known to those skilled in the art that are configured to convert the one or more images from a projection space domain to an image space domain. For example, in one embodiment (e.g., where the object is viewed from merely one perspective) backprojection techniques known to those skilled in the art are used. In another embodiment (e.g., where the object is viewed from a plurality of perspectives), tomosynthesis techniques known to those skilled in the art may be used. It will be appreciated that by using tomosynthesis, for example, a multitude of images may be generated such that at least two different planes within the object may be represented by the images. That is, a first image may represent a first plane within the object and a second image may represent a different plane within the object. Thus, the object may be divided into one or more horizontal slices, and respective images may represent one of the slices, for example.

In the example method 600, ultrasound data indicative of a focus on a first slice of the object is used to generate an ultrasound image(s) depicting the selected plane within the object under examination at 614. That is, an ultrasound image(s) is generated which has spatial coincidence with a radiographic image generated at 612 in the example method 600.

The ultrasound images are generated from the ultrasound projection data using techniques known to those skilled in the art (e.g., techniques for converting from projection space to image space). It will be appreciated to those skilled in the art that to generate an ultrasound image depicting a plane that substantially corresponds to a plane of a radiographic image, a focusing of the ultrasound data may be adjusted such that it resides within a portion of the object represented by the radiographic image (e.g., the focus of the ultrasound data is adjusted to be comprised within the horizontal slice of the object that is represented by the radiographic image). Thus, the focus of the ultrasound image is centered on the slice that is depicted in the radiographic image. Such an adjustment may come during the ultrasound examination and/or during the conversion of the ultrasound data from projection space to image space (e.g., the adjustment may come after the examination is complete and the object is no longer at the examination facility).

For example, in one embodiment, a first radiographic image that depicts a first plane within the object may be generated based upon information acquired from the radiographic examination at 612. Focusing of the ultrasound data may then be adjusted to correspond to the first plane within the object (e.g., such that a focus of the image is on a slice of the object represented by the first plane), and a first ultrasound image may be generated depicting the first plane within the object at 614. Focusing of the ultrasound data may then be adjusted again to correspond to a second plane within the object (e.g., depicted in a second radiographic image of the object generated at 612), and a second ultrasound image may be generated depicting the second plane within the object. In this way a multitude of ultrasound images that respectively depict substantially the same geometric positionings (e.g., horizontal slices) as a multitude of radiographic images may be generated.

It will be appreciated that by generating one or more ultrasound images that depict a substantially same portion of the object (e.g., geometric position) as one or more radiographic images, spatial coincidence between the ultrasound image(s) and the radiographic image(s) is formed. That is, a plane of at least one radiographic image, created from data acquired by from the radiographic modality, corresponds to a plane of an ultrasound image, created from data acquired by the ultrasound modality, in such a way that the ultrasound image may be overlaid onto the radiographic image or vice-versa. It will be appreciated that such coincidence is not attainable with disparate equipment (e.g., separate radiographic and ultrasound acquisition devices) when images are taken under different positioning conditions, for example. Similarly, such coincidence would likewise not be attainable where the object under examination is repositioned in a combined radiographic and ultrasound system (e.g., a single device is used, but data acquisition occurs at different times) because the orientation of the object would be, at least, slightly different when the different data is acquired.

In the example method 600, a radiographic image(s) depicting the selected plane within the object is combined with an ultrasound image(s) depicting the selected plane within the object to yield a combined image (e.g., 120 in FIG. 1) depicting the selected plane of the object in two examination modalities using techniques known to those skilled in the art at 616. In this way, images from two different modalities may be combined into a single image. That is, the sensitivity of an ultrasound image may be combined with the morphological details of a radiographic image (e.g., of a tomosynthesis image) to generate a combined image that provides useful information to a user viewing the image, for example. In one example, this may provide doctors with additional data, such as what is below and above a mass depicted in a radiographic image, for example, to assist in determining whether a mass is malignant or benign.

It will be appreciated that while the example method 600 provides for combining information from an ultrasound image with information from a radiographic image to generate a combined image, in another embodiment, the images for the two modalities are not combined. That is, a human user manually compares a radiographic image with an ultrasound image representing the same or similar plane within the object, for example.

The example method 600 ends at 618.

Figure 7:
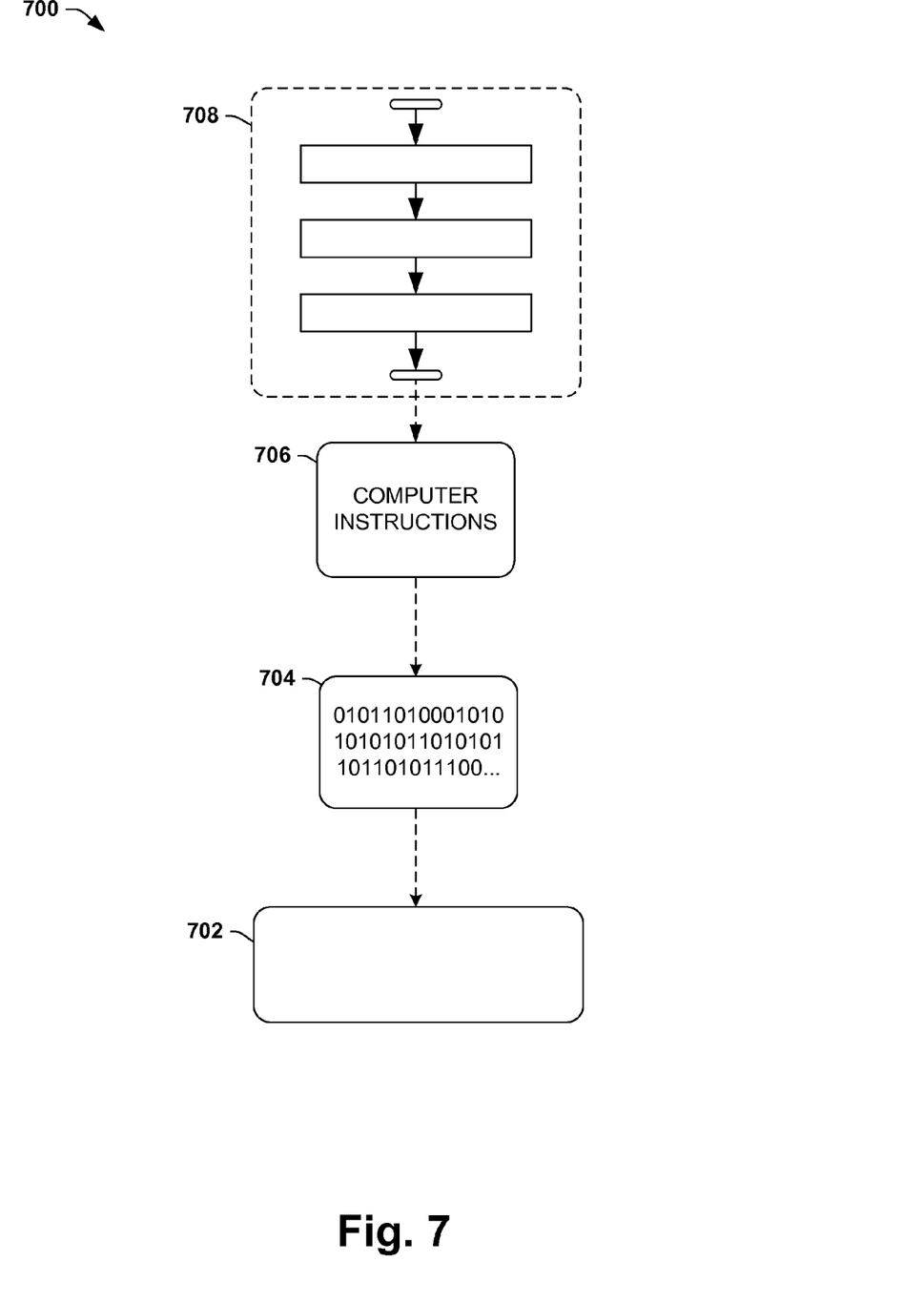
FIG. 7 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 7, wherein the implementation 700 comprises a computer-readable medium 702 (e.g., a flash drive, CD-R, DVD-R, or a platter of a hard disk drive), on which is encoded computer-readable data 704. This computer-readable data 704 in turn comprises a set of computer instructions 706 configured to operate according to one or more of the principles set forth herein. In one such embodiment 700, the processor-executable instructions 706 may be configured to perform a method 708, such as at least some of the example method 600 of FIG. 6, for example. In another such embodiment, the processor-executable instructions 706 may be configured to implement a system, such as at least some of the exemplary system 100 of FIG. 1, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An examination apparatus comprising:
    a radiation source configured to emit radiation;
    a detector array configured to detect radiation that has traversed an opening into which an object under examination is received while under examination;
    a guide mechanism for rotating the radiation source relative to the opening and relative to the detector array, wherein the detector array remains in a fixed position while the radiation source is being rotated using the guide mechanism;
    an ultrasound frontend component configured to transmit ultrasound waves into the object and to detect ultrasound waves reflected by the object while under examination;
    an immobilization device disposed between the radiation source and the opening and configured to substantially immobilize the object while under examination, the immobilization device defining a plurality of openings, wherein:
        a first portion of the ultrasound frontend component is sized to be received within a first opening of the plurality of openings,
        a second portion of the ultrasound frontend component is sized to be received within a second opening of the plurality of openings, and
        a third portion of the ultrasound frontend component is sized to rest on a top surface of the immobilization device, wherein:
            the third portion extends between the first portion of the ultrasound frontend component and the second portion of the ultrasound frontend component to bridge the first portion of the ultrasound frontend component with the second portion of the ultrasound frontend component and to concurrently suspend both the first portion of the ultrasound frontend component and the second portion of the ultrasound frontend component within the first opening and second opening while the object is under examination;
    an image reconstructor configured to generate a set of images of the object based upon the radiation detected by the detector array, a first image depicting a first cross-sectional slice of the object parallel to the top surface of the immobilization device and a second image depicting a second cross-sectional slice of the object parallel to the first cross-sectional slice of the object; and
    an ultrasound subsystem configured to generate an ultrasound image based upon detected ultrasound waves.

2. The examination apparatus of claim 1, wherein the immobilization device comprises a compression paddle and the detector array serves as a second compression paddle, the opening defined by the compression paddle and the detector array.

3. The examination apparatus of claim 1, wherein the image reconstructor is configured to generate the first image and the second image using tomosynthesis.

4. The examination apparatus of claim 1, wherein the radiation source is an ionizing radiation source.

5. The examination apparatus of claim 1, wherein the immobilization device-comprises one or more compression paddles configured to compress the object while the ultrasound frontend component transmits the ultrasound waves and while the radiation source emits the radiation.

6. The examination apparatus of claim 1, wherein the ultrasound image depicts a substantially same plane as the first cross-sectional slice.

7. The examination apparatus of claim 1, comprising:
an image combiner configured to spatially coincide the ultrasound image with the first image.

8. The examination apparatus of claim 1, comprising an ultrasound positioning system configured to position the first portion of the ultrasound frontend component within the first opening of the plurality of openings.

9. An examination apparatus comprising:
a radiation source configured to emit radiation;
a detector array configured to detect radiation that has traversed an opening into which an object under examination is received while under examination;
an ultrasound frontend component configured to transmit ultrasound waves into the object and to detect ultrasound waves reflected by the object while under examination;
an immobilization device disposed between the radiation source and the opening and configured to substantially immobilize the object, wherein:
the immobilization device defines a plurality of openings extending from a top surface of the immobilization device to a bottom surface of the immobilization device;
a first portion of the ultrasound frontend component is disposed within a first opening of the plurality of openings when the ultrasound frontend component is in use;
a second portion of the ultrasound frontend component is disposed within a second opening of the plurality of openings when the ultrasound frontend component is in use; and
a third portion of the ultrasound frontend component rests on the top surface of the immobilization device when the ultrasound frontend component is in use, wherein:
the third portion extends between the first portion of the ultrasound frontend component and the second portion of the ultrasound frontend component to bridge the first portion of the ultrasound frontend component with the second portion of the ultrasound frontend component and to concurrently suspend both the first portion of the ultrasound frontend component and the second portion of the ultrasound frontend component within the first opening and second opening while the object is under examination;
an image reconstructor configured to generate an image based upon the radiation detected by the detector array, the image depicting a first cross-sectional slice of the object parallel to the top surface of the immobilization device;
an ultrasound subsystem configured to generate an ultrasound image based upon detected ultrasound waves; and
an image combiner configured to spatially coincide the ultrasound image with the image.

10. The examination apparatus of claim 9, wherein the immobilization device comprises one or more compression paddles configured to compress the object.

11. The examination apparatus of claim 9, comprising a guide mechanism for rotating the radiation source relative to the opening and relative to the detector array, wherein the detector array remains in a fixed position while the radiation source is being rotated using the guide mechanism.

12. The examination apparatus of claim 9, the image reconstructor configured to generate a second image based upon the radiation detected by the detector array, the second image depicting a second cross-sectional slice of the object parallel to the first cross-sectional slice.

13. A method of acquiring data from two imaging modalities regarding an object under examination, comprising:
performing a first examination on the object via radiation emitted by a radiation source while the object is immobilized by an immobilization device, wherein during the first examination a position of the radiation source is varied relative to a position of a detector array detecting the radiation;
generating an image based upon the first examination, the image depicting a first cross-sectional slice of the object parallel to a top surface of the immobilization device;
inserting a first portion of an ultrasound frontend component into a first opening of a plurality of openings defined within a top surface of the immobilization device facing the radiation source and a second portion of the ultrasound frontend component into a second opening of the plurality of openings while resting a third portion of the ultrasound frontend component that bridges the first portion of the ultrasound frontend component with the second portion of the ultrasound frontend component on the top surface of the immobilization device to concurrently suspend both the first portion of the ultrasound frontend component and the second portion of the ultrasound frontend component within the first opening and the second opening; and
performing a second examination on the object via ultrasound waves using the ultrasound frontend component;
generating an ultrasound image based upon the second examination; and
spatially coinciding the ultrasound image with the image.

14. The method of claim 13, comprising:
securing the object in a first orientation;
performing the first examination;
performing the second examination; and
unsecuring the object from the first orientation after both the first examination and the second examination have been performed.

15. The method of claim 13, comprising emitting the radiation from a plurality of directions relative to the object under examination.

16. The method of claim 13, comprising fusing the ultrasound image with the image based upon a spatial coincidence determined by spatially coinciding the ultrasound image with the image.

17. The method of claim 13, comprising:
generating a second image based upon the first examination, the second image depicting a second cross-sectional slice of the object different than the first cross-sectional slice; and generating a second ultrasound image based upon the second examination, the second ultrasound image depicting the second cross-sectional slice of the object.

18. The method of claim 17, wherein the image and the second image are generated using tomosynthesis.

19. The method of claim 13, wherein the first portion of the ultrasound frontend component is a first ultrasound transducer and the second portion of the ultrasound frontend component is a second ultrasound transducer.

20. The method of claim 13, the performing a first examination and the performing a second examination comprising performing the first examination and the second examination while the object is under compression using the immobilization device.

* * * * *